US00PP22215P2

(12) United States Plant Patent
Hartman

(10) Patent No.: US PP22,215 P2
(45) Date of Patent: Oct. 25, 2011

(54) ***CALADIUM* PLANT NAMED 'WHITE DIAMOND'**

(50) Latin Name: *Caladaium×hortulanum*
Varietal Denomination: White Diamond

(76) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 12/800,180

(22) Filed: May 10, 2010

(51) Int. Cl.
*A01H 5/00* (2006.01)

(52) U.S. Cl. ..... Plt./373

(58) Field of Classification Search ..... Plt./373
See application file for complete search history.

*Primary Examiner* — June Hwu
(74) *Attorney, Agent, or Firm* — C. A. Whealy

(57) ABSTRACT

A new and distinct cultivar of *Caladium* plant named 'White Diamond', characterized by its upright and mounding plant habit; short to intermediate plant size; uniform potted plant habit with or without de-eyeing tubers; vigorous and dense growth habit; fast growth rate; and lance-type leaves that are white to green with few light pink-colored spots, dark green-colored margins and white-colored venation.

5 Drawing Sheets

Botanical designation: *Caladium×hortulanum.*
Cultivar denomination: 'WHITE DIAMOND'.

BACKGROUND OF THE INVENTION

The present invention relates to a new and distinct cultivar of *Caladium* plant, botanically known as *Caladium×hortulanum*, commercially referred to as a lance leaf-type *Caladium* and hereinafter referred to by the name 'White Diamond'.

The objective of the Inventor's breeding program is to create new *Caladium* plants that have uniform plant habit, exceptional container and garden performance and attractive foliage coloration.

The new *Caladium* plant originated from a cross-pollination made by the Inventor in April, 2002, in Lake Placid, Fla. of *Caladium×hortulanum* 'Lance Whorton', not patented, as the female, or seed, parent with *Caladium×hortulanum* 'Jackie Suthers', not patented, as the male, or pollen, parent. The new *Caladium* plant was discovered and selected by the Inventor as a single plant within the progeny of the stated cross-pollination in a controlled outdoor nursery environment in Lake Placid, Fla. on Jun. 15, 2003.

Asexual reproduction of the new *Caladium* plant by tuber divisions in a controlled outdoor nursery environment in Lake Placid, Fla. since Apr. 15, 2004 has shown that the unique features of this new *Caladium* plant are stable and reproduced true to type in successive generations of asexual reproduction.

SUMMARY OF THE INVENTION

Plants of the new *Caladium* have not been observed under all possible environmental conditions. The phenotype may vary somewhat with variations in environment such as temperature and light intensity, without, however, any variance in genotype.

The following traits have been repeatedly observed and are determined to be the unique characteristics of 'White Diamond'. These characteristics in combination distinguish 'White Diamond' as a new and distinct *Caladium* plant:

1. Upright and mounding plant habit; short to intermediate plant size.
2. Uniform potted plant habit with or without de-eyeing tubers.
3. Vigorous and dense growth habit.
4. Fast growth rate.
5. Lance-type leaves that are white to green with few light pink-colored spots, dark green-colored margins and white-colored venation.

Plants of the new *Caladium* differ primarily from plants of the female parent, 'Lance Whorton', in the following characteristics:

1. Plants of the new *Caladium* grow faster than plants of 'Lance Whorton'.
2. Plants of the new *Caladium* and 'Lance Whorton' differ in leaf coloration as plants of 'Lance Whorton' have pink to red-colored leaves with green-colored sectors, pink-colored splotches, green-colored margins and red-colored venation.

Plants of the new *Caladium* differ primarily from plants of the male parent, 'Jackie Suthers', in leaf coloration as plants of 'Jackie Suthers' have white-colored leaves with a pink blush, green-colored margins and white-colored venation.

Plants of the new *Caladium* can be compared to plants of 'White Wing', not patented. In side-by-side comparisons conducted in Lake Placid, Fla., plants of the new *Caladium* differed primarily from plants of 'White Wing' in the following characteristics:

1. Plants of the new *Caladium* grew faster than plants of 'White Wing'.
2. Plants of the new *Caladium* had broader leaves than plants of 'White Wing'.
3. Plants of the new *Caladium* and 'White Wing' differed in leaf coloration as plants of 'White Wing' had white to grey silver-colored leaves with green-colored mottled margins and pink to creamy white-colored venation.

Plants of the new *Caladium* can also be compared to plants of 'White Marble', disclosed in U.S. Plant Pat. No. 18,819. In side-by-side comparisons conducted in Lake Placid, Fla., plants of the new *Caladium* differed primarily from plants of 'White Marble' in the following characteristics:

1. Plants of the new *Caladium* grew faster than plants of 'White Marble'.
2. Plants of the new *Caladium* were shorter than plants of 'White Marble'.
3. Plants of the new *Caladium* had broader leaves than plants of 'White Marble'.

BRIEF DESCRIPTION OF THE PHOTOGRAPHS

The accompanying photographs illustrate the overall appearance of the new *Caladium* plant. These photographs show the colors as true as it is reasonably possible to obtain in colored reproductions of this type.

Colors in the photographs may differ slightly from the color values cited in the detailed botanical description which accurately describe the colors of the new *Caladium* plant.

The photograph on the first sheet is a side perspective view of a typical plant of 'White Diamond' grown in a container in a shadehouse.

The photograph on the second sheet is a close-up view of typical inflorescences and leaves of 'White Diamond'.

The photograph at the top of the third sheet is a top perspective view of typical plants of 'White Diamond' grown in an outdoor nursery.

The photograph at the bottom of the third sheet is a close-up view of typical freshly-dug tubers and roots of 'White Diamond'.

The photograph at the top of the fourth sheet is a side perspective view of typical potted plants of 'White Diamond' grown from de-eyed tubers (left) and 'White Diamond' grown from tubers that were not de-eyed (right).

The photograph at the bottom of the fourth sheet is a side perspective view of typical potted plants of 'White Diamond' (left) and the male parent, 'Jackie Suthers' (right).

The photograph at the top of the fifth sheet is a side perspective view of typical potted plants of the female parent, 'Lance Whorton' (left), 'White Diamond' (center) and 'White Wing' (right).

The photograph at the bottom of the fifth sheet is a side perspective view of typical potted plants of 'White Wing' (left) and 'White Diamond' (right).

DETAILED BOTANICAL DESCRIPTION

The aforementioned photographs and following observations and measurements describe plants grown during the spring and summer in 15-cm containers in Avon Park, Fla. in a polypropylene-covered shadehouse (30% shade) and plants grown during the spring and summer in ground beds in Zolfo Springs, Fla. during the late summer and autumn in an outdoor nursery. All plants were grown under conditions and practices which approximate those generally used in commercial *Caladium* production. During the production of the plants, day temperatures ranged from about 20° C. to 35° C., night temperatures ranged from about 10° C. to 26° C. and light levels were about 8,000 foot-candles (shadehouse) or 10,000 to 12,000 foot-candles (outdoor nursery). Plants had been growing in the shadehouse for four weeks from planting tubers when the photographs and the detailed description were taken. Plants had been growing in the outdoor nursery for six months from planting tuber divisions when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'White Diamond'.

Parentage:

*Female, or seed, parent.*—*Caladium×hortulanum* 'Lance Whorton', not patented.

*Male, or pollen, parent.*—*Caladium×hortulanum* 'Jackie Suthers', not patented.

Propagation:

*Type.*—By tuber divisions.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented; individual segments ovate in shape. Height: About 4 cm. Diameter: About 5.3 cm. Texture: Thick and starchy; somewhat brittle. Color: Epidermis, between 174B and 176C to 176D; with development, close to 200A to 200B; interior, close to 155B to 10D. Root description: Dense, thick, fleshy contractile roots with few lateral branches; color, close to 155C.

Plant description:

*Plant type.*—Herbaceous perennial; suitable as a potted plant in containers 15-cm to 25-cm and also suitable as a landscape plant.

*Plant and growth habit.*—Upright and mounding plant habit; short to intermediate plant size; inverted triangle; vigorous and dense growth habit; rapid growth rate; petioles and leaves arise from one or more growing points on tubers; petioles mostly upright and leaning outwardly with development.

*Plant height, from soil level to top of leaf plane, shadehouse-grown plants.*—About 30 cm to 32 cm.

*Plant height, from soil level to top of inflorescences, shadehouse-grown plants.*—About 29 cm to 39 cm.

*Plant diameter or spread, shadehouse-grown plants.*—About 44 cm to 50 cm.

*Number of clumps per plant, shadehouse-grown plants.*—About ten to twelve from tubers.

*Cataphylls, shadehouse-grown plants.*—Length: About 5 cm to 8 cm. Width: About 1.5 cm. Shape: Lanceolate. Apex: Acute. Base: Sheathing the stem. Color, inner and outer surfaces: Close to 147D tinged with close to N170D variably streaked and speckled with close to 147A or close to N170D tinged with close to 147D, with development, color becoming closer to 199C.

Foliage description:

*Length, shadehouse-grown plants.*—About 15.5 cm to 19 cm.

*Width, shadehouse-grown plants* (*flattened*).—About 10 cm to 15.5 cm.

*Shape.*—Ovate.

*Apex.*—Acuminate.

*Base.*—Sagittate to sagittate-peltate.

*Margin.*—Entire; mostly flat with some broad undulations.

*Texture, upper surface.*—Smooth, glabrous.

*Texture, lower surface.*—Smooth, glabrous; glaucous.

*Venation pattern.*—Pinnate.

*Color, shadehouse-grown plants.*—Developing leaves, upper surface: Center: Diffuse areas of 147A to 147B, 146A and 137A; white, close to 155C, areas adjacent to veins and in intervenal areas; random spots, close to 155C. Margins: Between 147A and 137A; basal notch, close to 187B to 187C. Venation: Midrib, close to 192B; primary veins, between 147D and 191C or whiter than 155C. Developing leaves, lower surface: Center: Diffuse areas of 191A to 191B; white, close to 155C, areas adjacent to veins and in intervenal areas; random spots and sectors, close to 155C. Margins: Close to 191A; basal notch, close to 187C. Venation: Midrib, between 193A and 145C to 145D; primary veins, between 193A and 145C to 145D. Fully expanded leaves, upper surface: Center: Diffuse areas of 147A to 147B and 146A; white, close to 155B to 155C to more white than 155C, sectors and areas adjacent to veins and in intervenal areas; random spots, close to 155C or close to 155C tinged with close to 186C to 186D. Margins: Between 147A and 137A; basal notch, close to 187B to 187C. Venation: Midrib, close to 192C to 192D; primary veins, close to 192A. Fully expanded leaves, lower surface: Center: Diffuse areas of 191A to 191B and 147C; white, close to 155C and 192D, sectors and areas adjacent to veins and in intervenal areas; random spots, close to 155C or close to 155C tinged with close to 186C to 186D. Margins: Close to 191A; basal notch, close to 187C. Venation: Midrib, between 193A and 147D; primary veins, between 193B and 147D.

*Petiole.*—Aspect: Mostly erect, outwardly leaning and arching with development; flexible. Length, shadehouse-grown plants: About 27 to 32 cm. Diameter, distal, shadehouse-grown plants: About 3.8 mm. Diameter, proximal, shadehouse-grown plants: About 8 mm. Color, newly emerged petioles, shadehouse-grown plants: Close to 159C tinged with close to N170D and streaked and specked with close to 147A to 147B. Color, fully developed petioles, proximal, shadehouse-grown plants: Close to 147B to 147C streaked and speckled with darker than 147A. Color, fully developed petioles, distal, shadehouse-grown plants: Close to 147D streaked with close to 147A. Wing length, shadehouse-grown plants: About 6 cm. Wing diameter, shadehouse-grown plants: About 8 mm. Wing color, shadehouse-grown plants, outer and inner surfaces: Close to N170D tinged with close to 147C to 147D and streaked and speckled with close to 147A to 147B.

Inflorescence description: Inflorescences observed on shadehouse-grown plants.

*Inflorescence arrangement.*—Upright hooded spathes surrounding a columnar spadix borne on a tall upright scape; spadix with sessile, simple female and male flowers separated into two zones; female flowers arranged on the lower one-third of the spadix; male flowers arranged on the upper two-thirds of the spadix; sterile flowers develop between female and male flower zones; near this area, the spathe constricts and surrounds and encloses the female flowers; spathe open and cupped around male flowers.

*Fragrance.*—None detected.

*Natural flowering season/longevity.*—Plants of the new *Caladium* typically flower during the spring or early summer in central Florida; flowers develop about four weeks after growth commences; inflorescences last about three days before fading; inflorescences persistent.

*Spathe.*—Length: About 9.5 cm; open length, about 6 cm and closed length, about 3.5 cm. Width, distal: About 3.3 cm. Width, proximal: About 2.7 cm. Width, at constriction: About 1.7 cm. Shape: Ovate. Apex: Acute to acuminate. Base: Tapering to the peduncle. Margin: Entire. Texture, upper and lower surfaces: Smooth, glabrous. Color: Front surface: Upper two-thirds: Close to 155C and 159C tinged with close to 193B; color becoming closer to 199C and 159C with development. Lower one-third: Close to 137D streaked with close to 147C; color becoming closer to 137A to 137B variably mottled with close to 191A to 191B and 138B variably streaked with close to 157A and 193B with development. Rear surface: Upper two-thirds: Close to 149D variably mottled with close to 155C; color becoming closer to 155C and 159C tinged with close to 193B with development. Lower one-third: Close to 191A to 191B and 138B variably streaked with close to 157A and 193B. Spadix: Length: About 5.8 cm. Length, male flower zone: About 2.7 cm. Length, female flower zone: About 1.6 cm. Length, sterile flower zone: About 1.5 cm. Diameter, male flower zone: About 8 mm. Diameter, sterile flower zone: About 6.5 mm. Diameter, female flower zone: About 9 mm. Shape: Columnar. Apex: Obtuse to bluntly acute. Base: Obtuse. Aspect: Upright. Color, mature, male zone: Close to 159C to 159D. Color, mature, sterile zone: Close to 159C to 159D. Color, mature, female zone: Between 161C and 161D and 15D. Male flowers: Quantity per spadix: About 154. Shape: Obovate. Height: About 2.8 mm. Diameter: About 2 mm. Anther color: Close to 158C. Amount of pollen: Moderate. Pollen color: Close to 11D. Female flowers: Quantity per spadix: About 261. Shape: Obovate. Height: About 3.2 mm. Diameter: About 2 mm. Stigma color: Between 161C and 161D and 15D. Ovary color: Close to 155C. Scape: Length: About 20 cm to 26 cm. Diameter: About 5 mm. Strength: Sturdy; flexible. Aspect: Erect. Texture: Smooth, glabrous; glaucous. Color: Between 147D and 160D streaked with close to 147A and variably tinged with close to N200A; just below spathe, between 138B and 191B. Seed and fruit: Seed and fruit development have not been observed on plants of the new *Caladium*.

Disease/pest resistance: Plants of the new *Caladium* have been observed to be relatively tolerant to *Pythium* root rot and *Xanthomonas* leaf blight. Plants of the new *Caladium* have not been observed to be resistant to pests or other pathogens common to *Caladium* plants.

Temperature tolerance: Plants of the new *Caladium* have been observed to be tolerant to temperatures ranging from about 7° C. to about 40° C. and suitable for USDA Hardiness Zones 8A to 11.

It is claimed:

1. A new and distinct *Caladium* plant named 'White Diamond' as illustrated and described.

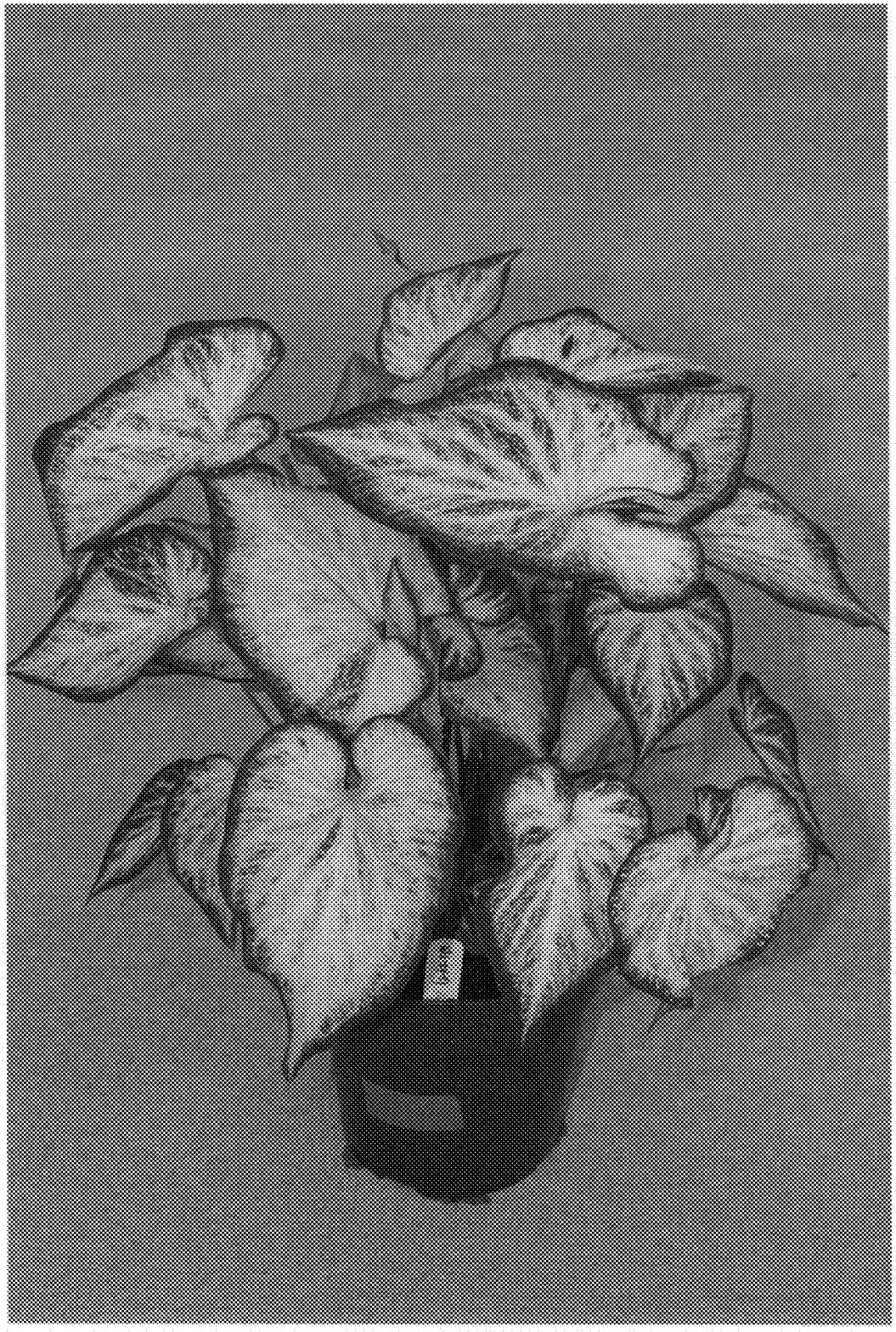

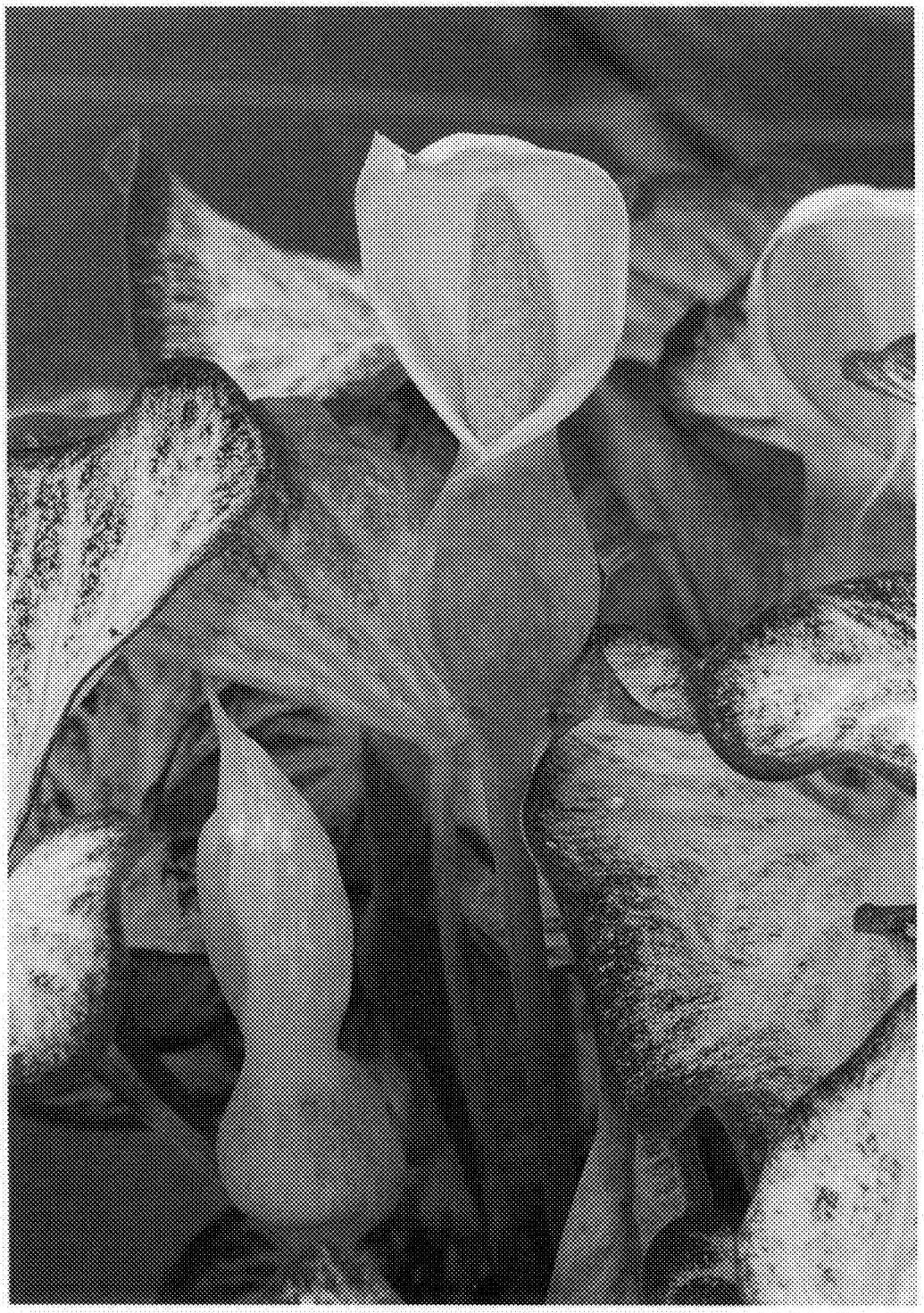

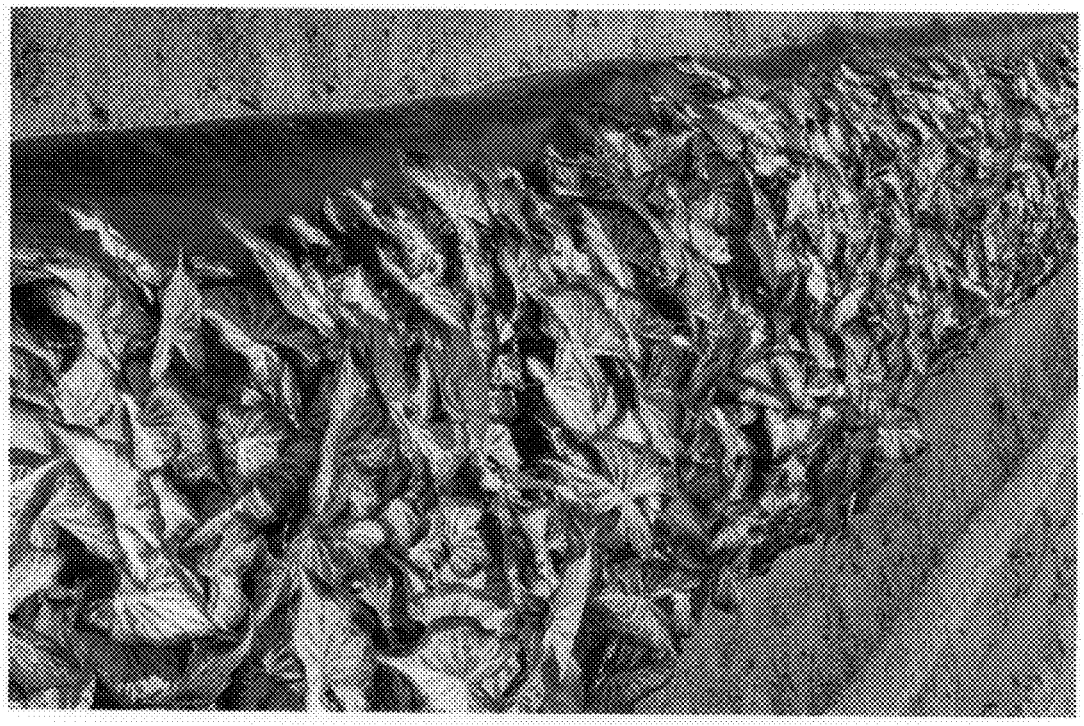
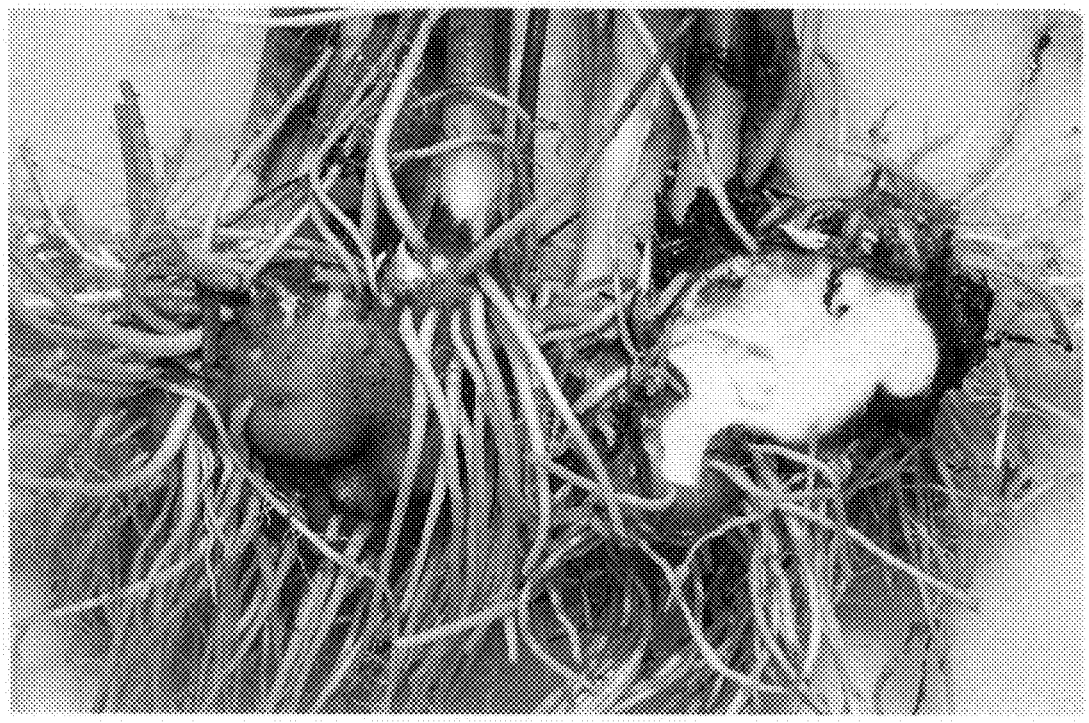

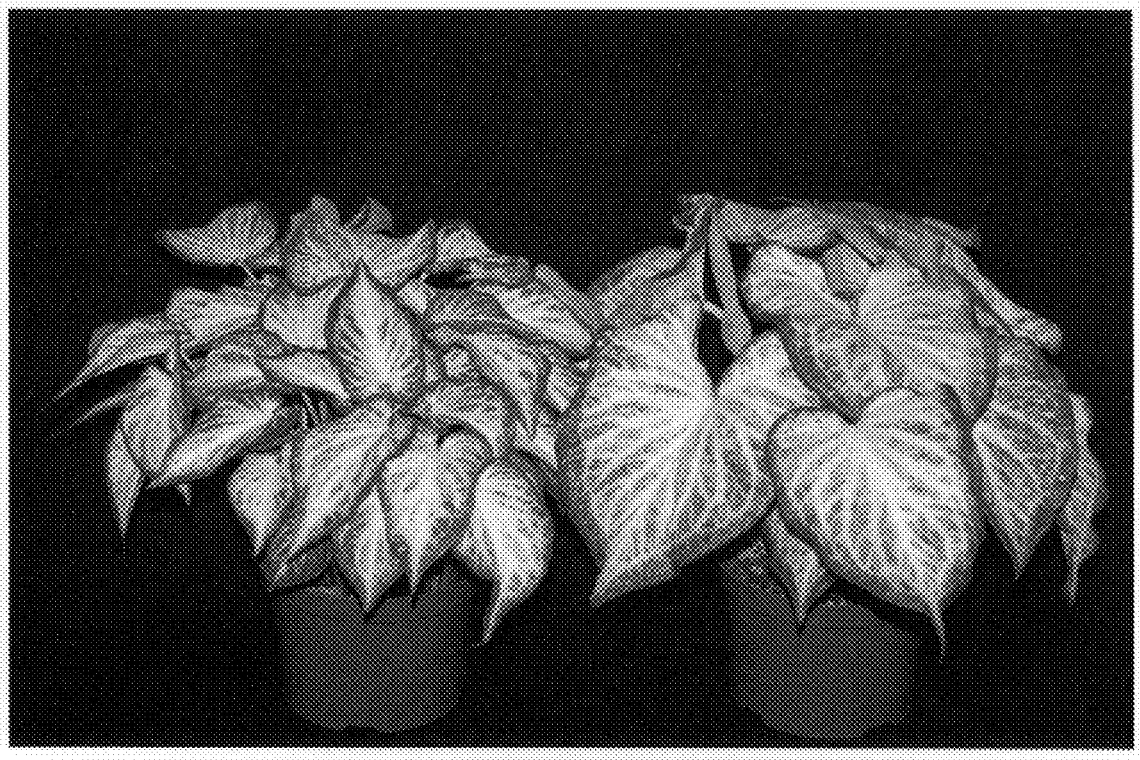
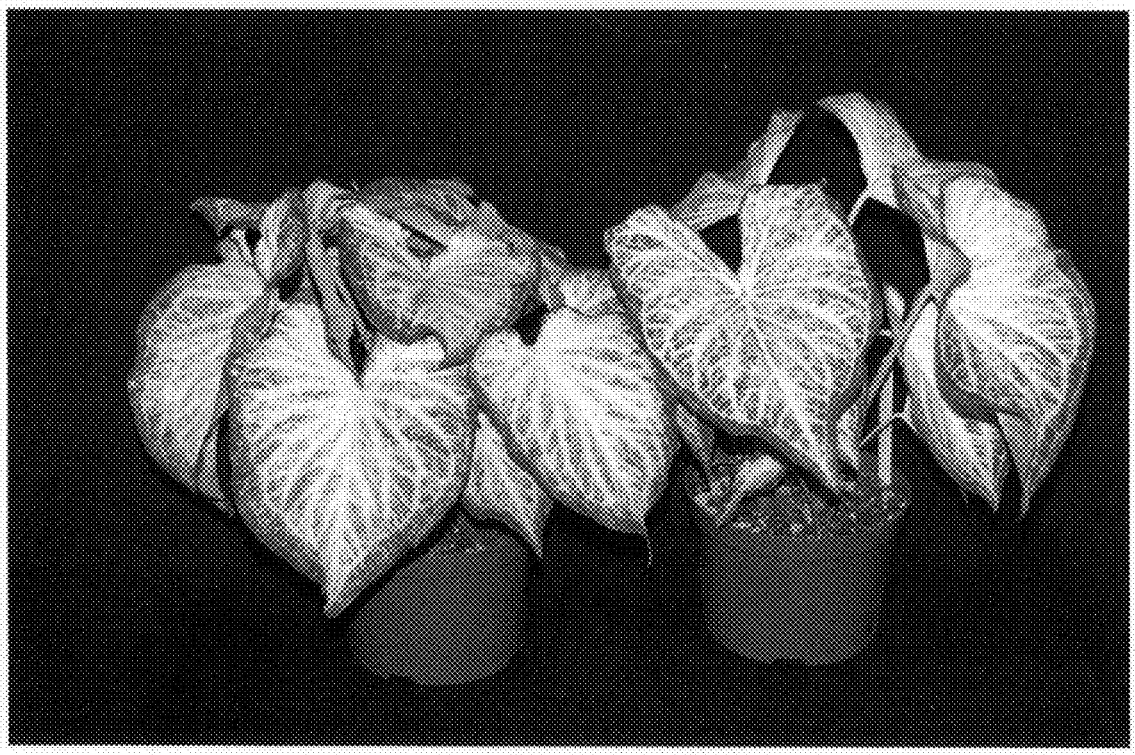

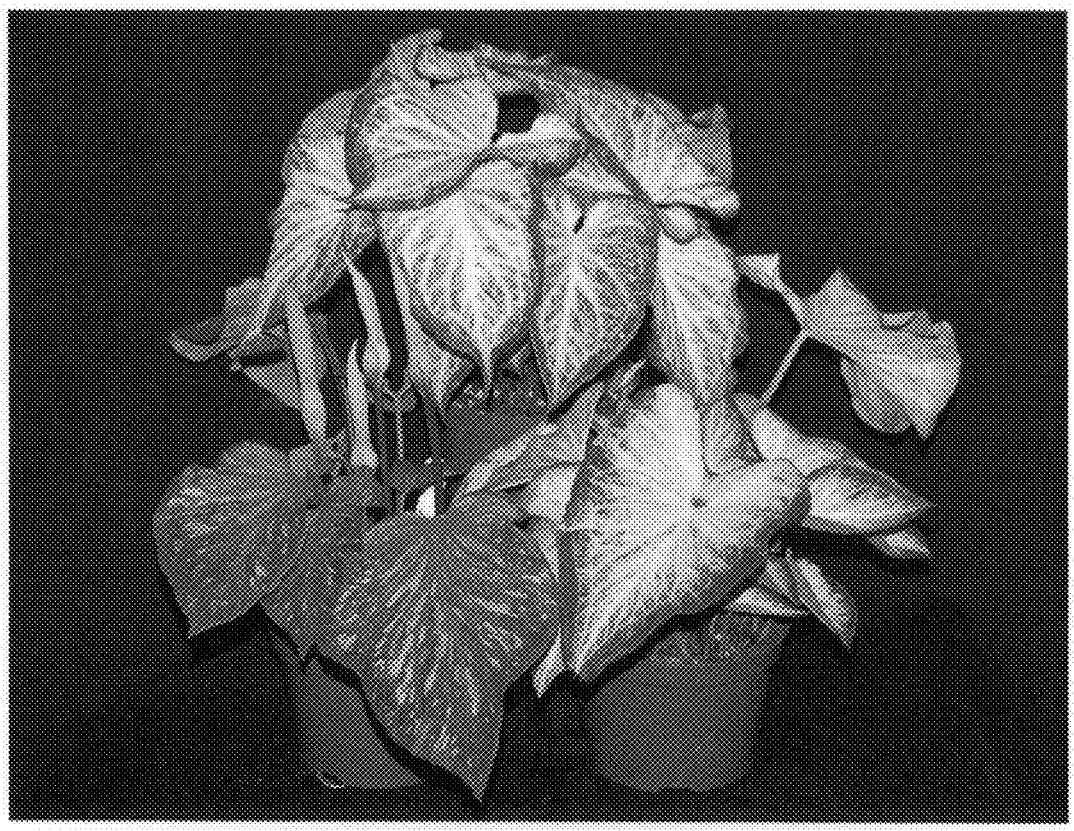
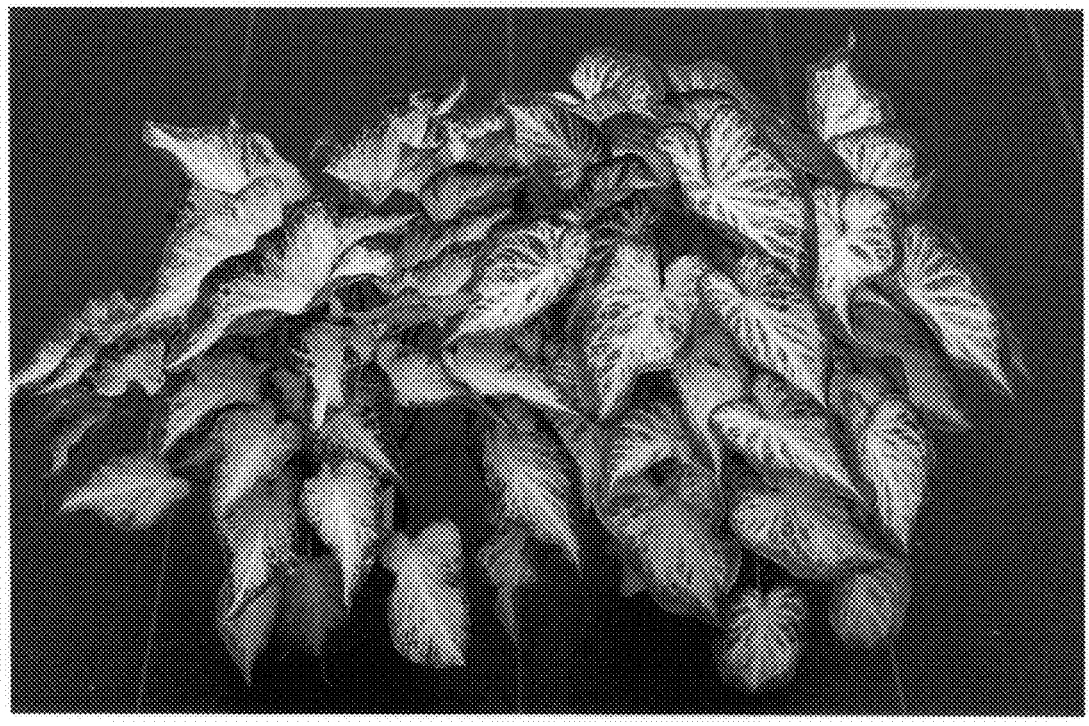

* * * * *